Figure 1:
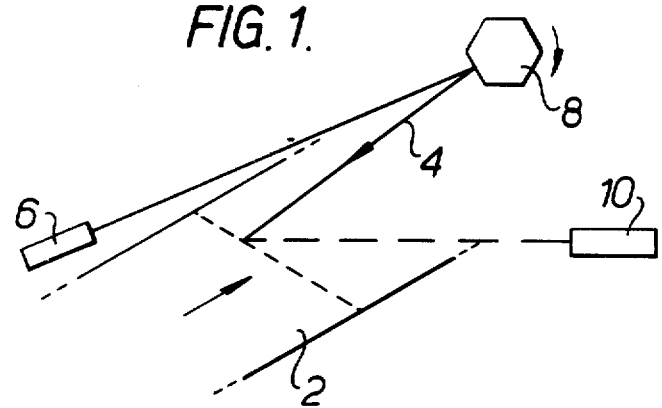

United States Patent [19]

Hill

[11] 4,298,808
[45] Nov. 3, 1981

[54] DEFECT DETECTION

[75] Inventor: Walter J. Hill, New Barnet, England

[73] Assignee: British Steel Corporation, London, England

[21] Appl. No.: 1,830

[22] Filed: Jan. 8, 1979

Related U.S. Application Data

[63] Continuation of Ser. No. 794,068, Jul. 20, 1978.

[30] Foreign Application Priority Data

May 10, 1976 [GB] United Kingdom ............ 19179/76

[51] Int. Cl.³ .......................................... G01N 21/88
[52] U.S. Cl. .................................. 250/563; 356/431
[58] Field of Search ............... 250/559, 562, 563, 571, 250/572, 550; 356/447, 448, 430, 431

[56] References Cited

U.S. PATENT DOCUMENTS

| | | |
|---|---|---|
| 3,803,420 | 4/1974 | Bossons ............................. 250/562 |
| 3,851,971 | 12/1974 | Koch .................................. 250/563 |
| 3,866,054 | 2/1975 | Wolf .................................. 250/563 |
| 4,110,048 | 8/1978 | Akutsu et al. ....................... 250/563 |

FOREIGN PATENT DOCUMENTS

| | | |
|---|---|---|
| 2400904 | 7/1974 | Fed. Rep. of Germany . |
| 2453865 | 5/1975 | Fed. Rep. of Germany . |
| 1045693 | 10/1966 | United Kingdom . |
| 1302865 | 1/1973 | United Kingdom . |

Primary Examiner—David C. Nelms
Attorney, Agent, or Firm—Bacon & Thomas

[57] ABSTRACT

A method for indicating a defect in a workpiece, comprises applying a continuously variable signal derived from inspection of the workpiece and including a pulse component representative of the defect to a bank of filters having different frequency transmission characteristics respectively representative of defects of different type so that the filter corresponding most closely to the defect inspected, produces a relatively greater output and provides an indication of defect type.

18 Claims, 4 Drawing Figures

DEFECT DETECTION

This is a continuation, of application Ser. No. 794,068, filed July 20, 1978.

This invention relates to the detection and the recognition of defects in materials and is particularly, although not exclusively, concerned with the detection and with the recognition of surface defects in metals.

The invention is particularly directed at the detection and the recognition of surface defects in steel strip moving at on-line velocities which preclude the use of conventinal visual techniques for detecting surface defects such as carbide and rolling inclusions, pitting and the like.

It has been proposed to detect the presence of surface defects in moving metal strip by scanning the strip transversely of the feed direction by a beam of light and detecting the light which is reflected from the surface and from any defect upon which the beam is incident during the scan. The beam is generally narrow such as that derived from a laser in order to increase resolution to an acceptable level, and is detected after reflection by a suitable photo-electric device such as a photomultiplier. To produce a scan which senses accurately across the true width of the strip rather than in an oblique direction, relatively high scanning speeds are employed, for example by means of a rapidly rotating mirror or prism disposed between the light source and the strip surface. High scanning speeds also ensure more complete cover of the strip surface and avoid the possibility that a defect will not be detected.

In conventional practice the scanner operates at an angular velocity of the order of 10 milliseconds per revolution and at this speed the signal derived from a strip of one meter in width has a residue time of not more than 4 milliseconds. At this residence period visual examination of a display derived from the output of a photo-electric device becomes virtually impossible without resorting to complex devices such as storage tubes.

In addition the signal from the detector will contain components representative both of surface roughness and bad shape in addition to transient signals representative of different types of defect. These perturbations produce a composite signal from which a defect is difficult to identify and recognise. Coupled with the low transient period, this poses considerable problems and it is one object of the present invention to achieve a suitable defect identification and recognition system.

According to its broadest aspect, the present invention provides a method for indicating a defect in a workpiece, the method comprising applying a continuously variable signal derived from inspection of the workpiece and including a pulse component representative of the defect to a bank of filters having different frequency transmission characteristics respectively representative of defects of different type so that the filter corresponding most closely to the defect inspected, produces a relatively greater output and provides an indication of defect type.

Suitable inspection is produced by scanning the workpiece with radiation which subsequently is incident upon a sensor effective to produce the signal including the defect pulse.

Alternatively, however, the workpiece may be substantially uniformly irradiated and inspection produced by providing scanned access of the workpiece to the sensor effective to provide the signal including the defect pulse. In this case the sensor itself may be moved to produce scanning, or may be arranged to receive radiation from the workpiece by way of an intermediate scanner, for example an optical system where the irradiation is light.

Suitably, a signal derived from the output of the filter bank pulse is compared with the filter pulse input to identify the defect.

In a preferred embodiment of the invention the composite signal representative of the surface of the workpiece under test is derived from the output of a photoelectric device arranged to receive light reflected by the surface from an incident scanning light beam. The composite output from the device will contain continuously variable components respectively representative of surface roughness and bad shape as well as transient components representative of discrete defects upon which the scanning beam is temporarily incident. A defect component applied to the bank of filters will correspond most closely with one of the filters if these have, by previous trail, been selected to correspond to the anticipated range of defect types likely to be encountered in the workpiece under test. The filter displaying the greatest correspondence will provide the greatest output if the overall gain of each of the filters in the bank are arranged to be equal.

The outputs of the filters may in one embodiment of the invention be applied directly to means such as digital voltmeters by which the respective outputs can be held for a time interval sufficient for the greatest output to be identified. With the transmission characteristics of that filter corellated to the type of defect, both defect identification and recognition can be achieved.

In a preferred embodiment of the invention the outputs from the filters in the bank are simultaneously applied to a largest value detector effective to identify only that filter producing the largest output. Ideally, the largest value detector produces a binary output and operates only in excess of a limiting threshold level which ensures that only transients in the composite signal which are representative of significant defects rather than surface irregularities are identified.

In the case where a largest value detector is employed, signals from the filters in the bank should be applied without any relative time delay. Since the filters will have different frequency transmission characteristics to cover different types of defect, each filter will introduce its own inherent and different time delay. Accordingly, the signal applied to each filter is appropriately delayed to compensate for differences in inherent delay. Conveniently the delay is achieved by individual delay lines in the filter inputs or by a tapped delay line which introduces the greatest delay into the filter of fastest response.

Suitably, the output from each filter is also applied to a peak detector providing a preferably binary output which is used to trigger an 'AND' gate responsive to the output of the largest value detector. This ensures that the largest value signal produces an output which has a defined time relationship with the defect signal irrespective of the time period during which the most closely matched filter produces the highest signal level.

The 'AND' gate when conducting operates a monostable pulse generator whose pulse length is matched to that of the corresponding filter and can be suitably displayed to indicate the type of defect detected.

Figure 2:
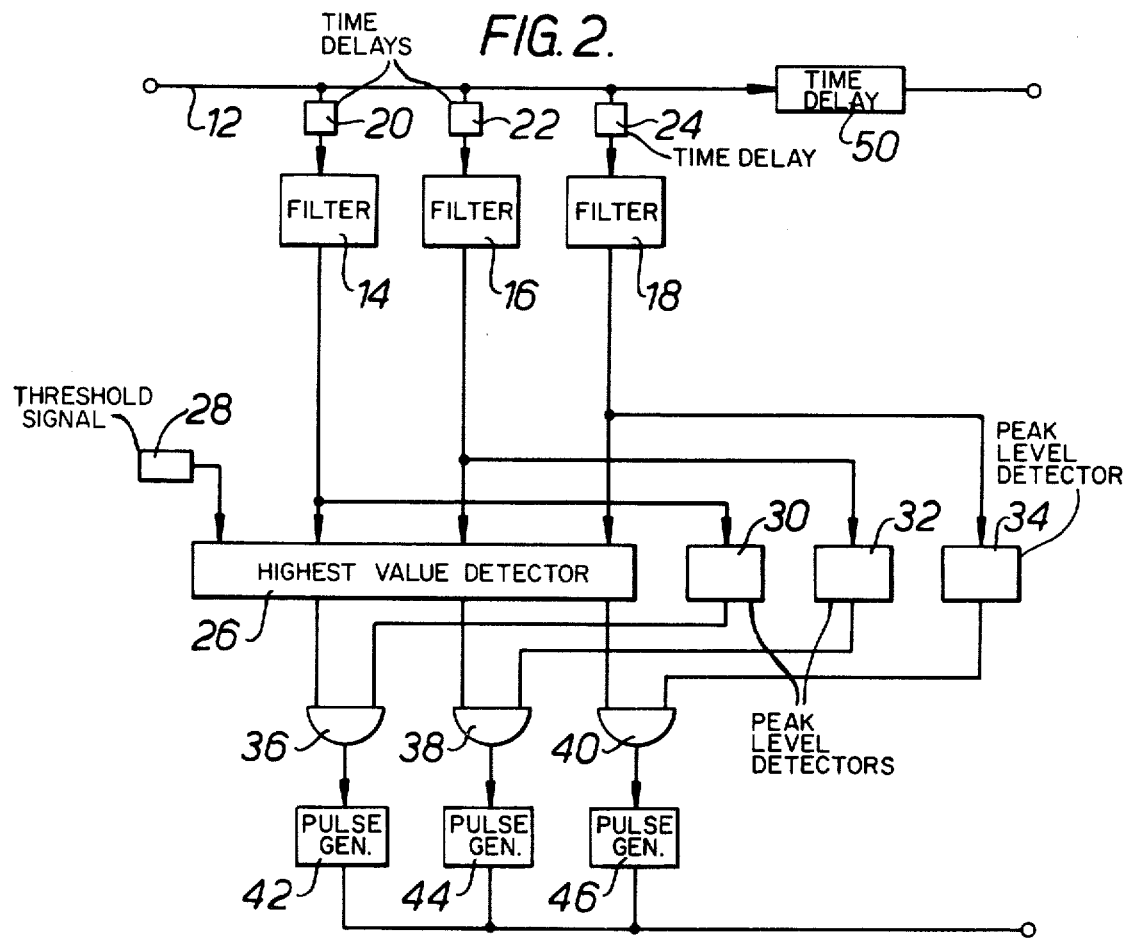

An embodiment of the invention will now be described by way of example with reference to the accompanying drawings in which FIG. 1 is a schematic representation of an arrangement for producing an electric signal representative of the surface of moving steel strip, FIG. 2 is a schematic diagram of a circuit for detecting and recognising defects in the strip of FIG. 1

Figure 3:
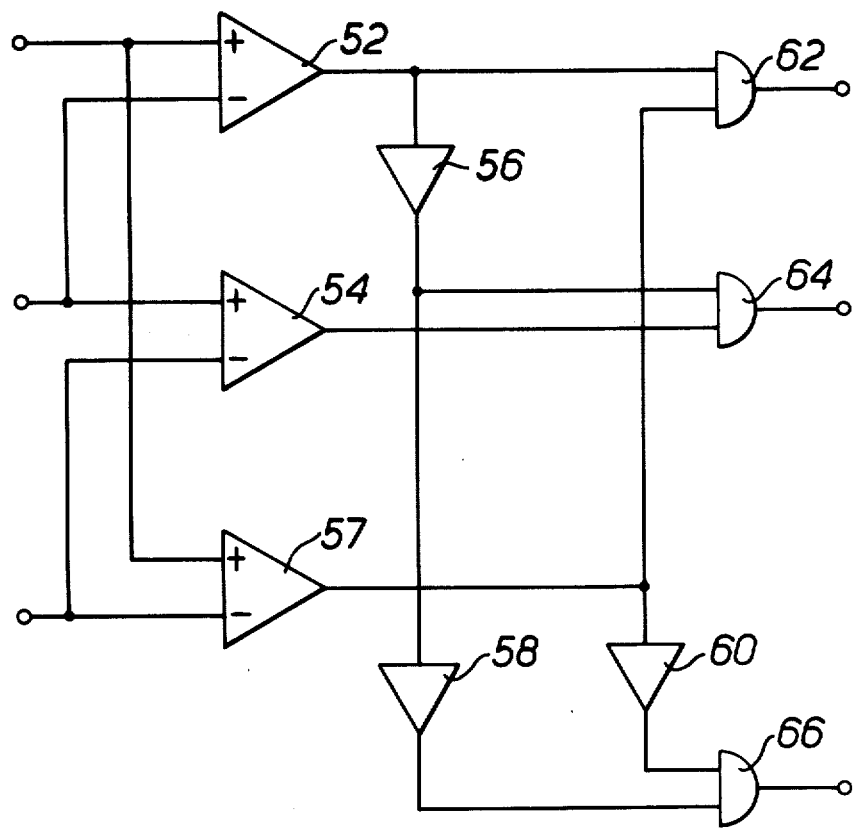
Figure 4:
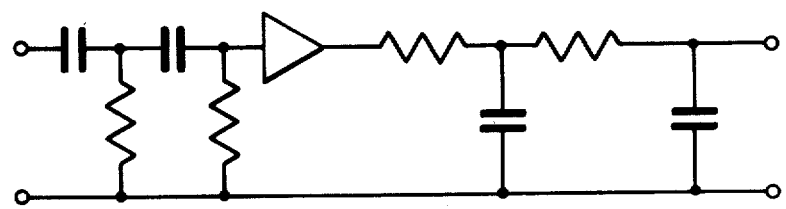

FIG. 3 is a circuit diagram of the largest value detector included in the circuit of FIG. 2 and FIG. 4 is a circuit diagram of a typical filter used in the circuit of FIG. 2.

Referring to FIG. 1, this schematically illustrates a strip of steel moving at on-line velocity in a cold rolling mill and in the direction indicated by the arrow. The strip surface will include defects such as carbide rolling inclusions and the like which may render the strip unsuitable for sale and which must accordingly be identified and recognised so that if necessary the portion of the strip including the defect can be removed.

To detect defects present, the surface of strip 2 is scanned across its width by a monochromatic light beam 4 derived from a laser 6 and directed for incidence upon the strip by way of a symmetrical multifacet mirror 8 rotated at a speed effective to produce an adequate scanning velocity. A typical velocity produces a scan across one meter strip width of 10 milliseconds.

Light reflected from the scan is incident upon a photomultiplier 10 whose output will be a composite signal containing components respectively representative of surface roughness, bad shape, and other perturbations in addition to transient signals representative of defects or inclusions.

To identify the defects and recognise their types, the composite signal is applied to the circuit illustrated in FIG. 2.

In this circuit the composite signal from photomultiplier 10 enters at input 12 and is simultaneoulsy applied to a bank of bank-pass filters 14,16 and 18 by way of individual time delay elements 20,22, and 24.

Each of the filters, which may be of the type shown in FIG. 4, have a different frequency transmission characteristic selected to correspond to the transient signals likely to be produced by different defects in the moving strip 2. As shown, the filter illustrated comprises a series arrangement of low pass filter, buffer and high pass filter of conventional type, although alternative arrangements may be used. The filter having the slowest response will introduce the greatest inherent delay to the signal applied from input 12 and will accordingly be associated with the line of shortest delay so that the combined delay of each filter-line combination is identical.

The filter whose characteristics most closely match that of the defect signal will produce the greatest output.

The output signals from filters 14,16 and 18, now delayed to coincidence, are applied to a highest value detector 26 where they are compared with a selected threshold signal from source 28 and which selects the largest excess level to produce a binary output only from the channel corresponding to the filter of greatest output amplitude. The threshold level is selected to ensure that only signals representative of significant defects are applied for comparison.

The outputs from filters 14,16 and 18 are also simultaneously applied to peak level detectors 30,32,34 of the type well known in the art, and whose outputs are used to trigger 'AND' gates 36,38,40 responsive also to the output signals generated by detector 26.

The 'AND' gates when conducting trigger corresponding mono-stable pulse generators 42,44,46 whose pulse lengths relatively correspond to the transmission characteristics of filters 14,16 and 18 and which are accordingly representative of corresponding defect types. The outputs from the pulse generators are combined and passed for suitable display. The signal from a pulse generator is predominantly charcteristic of the size of the defect in the strip 2. However, other characteristics of the defect may be obtained by comparing the pulse generator output with the corresponding portion of the orginal signal derived from photomultiplier 10 and applied to the input filters 14,16 and 18. Coincidence between these signals may, as previously, be achieved by a further time delay element such as 50 shown in FIG. 2.

A suitable highest value detector is shown in FIG. 3. It comprises voltage comparators 52,54,57 of standard type connected between every pair of analogue inputs which receive signals from the filters 14,16, and 18.

The outputs from the comparators are processed by a logic network effective to decode the comparison results and thereby indicate the largest filter output. As shown in FIG. 3, the logic network comprises invertors 56,58 and 60 inter-connected with 'AND' gates 62,64,66 in a manner effective to produce the combination of logic operations necessary to select the highest signal level.

In use, the filter with the greatest output in excess of the detection threshold will trigger only one of the 'AND' gates 36,38 and 40 which 'AND' gate will in turn activate the corresponding pulse generator. The defect will accordingly be both identified and recognised if the characteristics of the filters have been correctly matched to represent defects.

The output of the mono-stable or the corresponding 'AND' gate may activate any suitable indicator whose read-out may be retained for a single scan or a selected number of scans, and subsequently cancelled.

Successive scans incident upon defects of different type will produce the greatest output in a different filter which will activate a different mono-stable and produce similar identification and recognition.

It will be appreciated that while the invention has been described with reference to the detection of surface defects it could be applied to the internal defects of a workpiece. In this case the workpiece may be scanned by ultrasonic or X-Ray beams which are suitably detected to produce a composite signal which may be processed to detect and recognise the defect in similar manner.

We claim:

1. A method for indicating a defect in a workpiece, the method comprising applying a continuously variable signal derived from insepection of the workpiece and including a pulse component representative of the defect to a bank of filters having different frequency transmission characteristics respectively representative of defects of different type so that the filter corresponding most closely to the defect inspected, produces a relatively greater output and provides an indication of defect type.

2. A method as claimed in claim 1 wherein inspection is produced by scanning the workpiece with radiation which subsequently is incident upon a sensor effective to produce the signal including the defect pulse.

3. A method as claimed in claim 1 wherein inspection is produced by providing scanned access of the workpiece, when irradiated, to a sensor effective to produce the signal including the defect pulse.

4. A method as claimed in claim 2 wherein the workpiece is scanned by a light beam, and a photo-electric device is arranged to receive light reflected from the workpiece surface.

5. A method as claimed in claim 3 wherein the workpiece is substantially uniformly illuminated and a photo-electric device is arranged to scan the workpiece.

6. A method as claimed in claim 3 wherein the workpiece is substantially uniformly illuminated and an optical system effective to direct light onto a photo-electric device is arranged to scan the workpiece.

7. A method as claimed in claim 1 wherein the outputs of the filters are applied to a greatest value detector.

8. A method as claimed in claim 7 wherein the signal applied to each filter is delayed to compensate for differences in the inherent filter delays.

9. A method as claimed in claim 8 wherein delay is produced by individual delay elements in the filter inputs.

10. A method as claimed in claim 8 wherein delay is produced by a delay line tapped to feed individual filters.

11. A method as claimed in claim 7 wherein the largest value detector is effective to produce binary outputs.

12. A method as claimed in claim 7 wherein the largest value detector is effective to operate above a threshold effective to select only pulses representative of a significant defect.

13. A method as claimed in claim 8, wherein a signal derived from the output of the filter bank is compared with the filter input to identify the defect.

14. A method as claimed in claim 13, wherein the outputs of the filters are applied to peak detectors arrange, together with the outputs of a greatest value detector, to trigger AND gates effective to operate monostable pulse generators providing outputs representative of defect size.

15. A method as claimed in claim 14, wherein the pulse applied to the filter bank is compared with the output of the pulse generators to further identify the defect.

16. A method as claimed in claim 15 wherein a time delay is used to produce substantial signal coincidence between the pulse input to the filter bank and to the output of the pulse generators.

17. A method as claimed in claim 8 wherein a plurality of pulses derived from a plurality of inspection scans of the workpiece are applied to the filter bank.

18. An apparatus for detecting a defect in the surface of a workpiece comprising in combination means for receiving a continuously variable electrical signal derived from inspectin of the surface of the workpiece and including a pulse component representative of the surface defect, said receiving means including a bank of a plurality of electrical filters each having different frequency transmission characteristics representative of different types of surface defects, and means for receiving signals from the outputs of the filter bank, identifying the filter producing the greatest output and indicating the type of surface defect corresponding to this filter.

* * * * *